(12) United States Patent
Koskinen et al.

(10) Patent No.: US 7,344,632 B2
(45) Date of Patent: Mar. 18, 2008

(54) PRODUCTION OF FUEL COMPONENTS

(75) Inventors: Matti Koskinen, Helsinki (FI); Petri Lindqvist, Porvoo (FI); Harri Jarvelin, Helsinki (FI)

(73) Assignee: Neste Oil OYJ, Espoo (FI)

( * ) Notice: Subject to any disclaimer, the term of this patent is extended or adjusted under 35 U.S.C. 154(b) by 332 days.

(21) Appl. No.: 10/953,293

(22) Filed: Sep. 28, 2004

(65) Prior Publication Data

US 2006/0065574 A1    Mar. 30, 2006

(51) Int. Cl.
*C10G 65/02* (2006.01)
*C07C 41/06* (2006.01)

(52) U.S. Cl. .................... 208/49; 568/697; 585/510

(58) Field of Classification Search ............... 568/697; 585/510
See application file for complete search history.

(56) References Cited

U.S. PATENT DOCUMENTS 3,979,461 A    9/1976  Ancillotti et al. ........... 568/697

6,011,191 A    1/2000  Di Girolamo et al. ...... 585/514

FOREIGN PATENT DOCUMENTS

| EP | 0590632 | A1 | 4/1994 |
| EP | 0994088 | A1 | 4/2000 |
| GB | 1173128 | | 12/1969 |
| GB | 2325237 | A | 11/1998 |

*Primary Examiner*—Rosalynd Keys
(74) *Attorney, Agent, or Firm*—Birch, Stewart, Kolasch & Birch, LLP

(57) ABSTRACT

A process for producing alkyl ethers, by etherification of tertiary $C_{4-7}$ olefins with an alkanol, comprising carrying out the etherification in reactor train system primarily configured for dimerization of isoolefins. In the etherification, the ratio of alkanol-to-olefin is 0.5 to 2, calculated from the amount of tertiary $C_{4-7}$ olefins of the fresh feedstock. The invention makes it possible to change the product of the process from dimer to ether and vice versa merely by adjusting specific flows within the process. The present kind of process is therefore readily adaptable to fluctuating market demands for various gasoline octane-boosters (isooctane or MTBE).

18 Claims, 1 Drawing Sheet

PRODUCTION OF FUEL COMPONENTS

BACKGROUND OF THE INVENTION

1. Field of the Invention

The present invention relates to the preparation of fuel components. In particular, the invention concerns a process for dimerizing and etherifying isoolefins in a reactor train system comprising, in a cascade, a primary reaction zone, a primary distillation zone, a secondary reaction zone and a secondary distillation zone.

2. Description of Related Art

Tertiary alkyl ethers are added to automotive fuels (gasoline) in order to improve the anti-knocking characteristics of the fuels without using organolead compounds and in order to reduce the concentration of detrimental components in the exhaust gases. The oxygen-containing ether group of these octane-booster compounds has been found to improve the combustion process favourably. Suitable alkyl tert-alkyl ethers are methyl t-butyl ether (MTBE), ethyl t-butyl ether (ETBE), t-amyl methyl ether (TAME), t-amyl ethyl ether (TAEE) and t-hexyl methyl ether (THME), just to mention a few examples. These ethers are prepared by etherification of a monovalent aliphatic alcohol with an isoolefin. These olefins include, but are not limited to isobutene, 2-methyl-1-butene (2M1B), 2-methyl-2-butene (2M2B), 2-methyl-1-pentene (2M1P), 2-methyl-2-pentene (2M2P) and 2,3-dimethyl-1-pentene (2,3DMP).

Processes for producing the above-mentioned ethers are disclosed in, e.g., U.S. Pat. Nos. 5,536,886, 5,637,777, 5,908,964, and 6,369,280.

The octane number of the automotive fuels can also be increased by adding other gasoline components, such as $C_4$-alkylates or isomerates. The alkylate is typically produced by alkylating isobutane and isobutene, whereby trimethylpentanes and dimethylhexanes are obtained. Furthermore, by dimerizing isobutene to isooctene, and optionally further hydrogenating it to isooctane, a component equal to or better than alkylate is obtainable. Isooctane/isooctene processes are discussed in, e.g., EP Patent Application No. 0 994 088, U.S. Pat. No. 6,011,191 and GB Patent No. 2 325 237.

Various processes of producing both olefin ethers and olefin dimers in the same reaction system are also known in the art. The reaction between an isoolefin and an alcohol is an equilibrium reaction which, depending on the reaction conditions, will yield an ether or a dimer, or (a mixture of) both. Thus, to mention an example, EP-A-0 745 576 discloses a process, in which MTBE and isooctene are produced simultaneously. According to the publication, the molar ratio of the alcohol and the isoolefin has to be primarily sub-stoichiometric or in the range of 0.2-0.7.

Another process for producing both $C_4$-oligomers and alkyl-t-butylether is known from EP-A-0 048 893. In that process, a high feed ratio of alcohol and isobutene is used. In the publication, reference is made to the possibility of recycling the product in order to produce longer oligomers.

EP-A-0 994 088 concerns an improved process for dimerizing iso-olefins, which employs a reactor train system including a reaction zone and a separation zone (e.g. a distillation column) connected to an effluent outlet of the reaction zone. The olefinic hydrocarbon feedstock is contacted with an acidic catalyst in the presence of an oxygenate at conditions in which at least a part of the olefins dimerizes, the effluent is conducted from the reaction zone to the separation zone, where dimerized reaction product is separated, and the reaction product is then recovered and, optionally hydrogenated. A side draw comprising unreacted olefins and alkanol is taken from the separation zone and recirculated to the reaction zone.

The process described in EP-A-0 994 088 is particularly advantageous because it allows for free selection of the product composition of the dimerizing unit and makes it possible to produce either pure dimer or a mixture of dimer and ether in the same unit.

Although the consumption of alkyl ethers as octane-boosters is decreasing in certain areas of the world, such as in California, many producers still wish to retain the option of using the same basic equipment for producing a dimer, such as isooctane/isooctene, and alkyl ethers, such as methyl-t-butyl ether or t-amylmethyl ether, depending on the demand on the market for the various fuel components. In particular, there is a need for ways of easy modification of the equipment used for dimerization of olefins so that it can be used for etherification of the olefins at high conversion rates.

SUMMARY OF THE INVENTION

It is an aim of the present invention to provide a process for producing in the same process equipment dimers, such as isooctane/isooctane, and alkyl ethers, in particular tert-methyl butyl ether, by appropriately adjusting the ratio of isoolefins to alkanol. Thus, the present invention provides a process in which, during a first predetermined time period, dimers are produced and then, during a second predetermined period of time, alkyl ethers are produced.

It is another aim of the present invention to provide a method of adapting a process equipment intended for dimerization of isobutene to etherifying isobutene.

These and other objects, together with the advantages thereof over the known processes, which shall become apparent from specification which follows, are accomplished by the invention as hereinafter described and claimed.

In the process of EP-A-0 994 088, sub-stoichiometric molar ratios between the alkanol and the olefin are recommended and a ratio of less than 0.2 is specifically suggested. According to the present invention, a dimerization process of the above kind can be converted to an etherification process by increasing the molar proportion of the alkanol in the first reaction zone to favour the formation of alkyl ether instead of dimer and by conducting the overhead of the separation zone to a second reaction zone, wherein the unreacted components of the feedstock, including alkanol and olefinic hydrocarbons, are subjected to a second etherification reaction. Such a secondary reaction zone can be included in the basic configuration of the dimerization process already.

Accordingly, in an embodiment of the known dimerization process, in order to produce ethers, the isoolefinic feed is combined with an alkanol (alkyl alcohol) in or before a first reaction zone and subjected to a first etherification reaction, a reaction effluent is withdrawn and conducted to a first distillation column. An alcohol-containing flow is drawn from the side of the first distillation column and recirculated to the first reaction zone, whereas the overhead product is conducted to a second reaction zone. There, the product is subjected to a second etherification reaction. The reaction effluent is introduced into a second distillation column. The bottoms products of the first and second distillation columns comprise essentially pure alkyl ether and are combined, whereas the overhead of the second distillation column, comprising unreacted hydrocarbons and alkanol, is subjected to washing to separate the alkanol.

According to the present invention, by using as sufficiently high molar ratio between the alkanol and the isoolefins, alkyl ether will be produced at high conversion rates. Generally the ratio of alkanol to reactive olefin is higher than 0.7, preferably at least 0.8 and up to 2.0 at the most, advantageously about 0.8 to 1.5, and in particular in excess of 0.9 up to about 1.1. The expression "reactive olefins" refers to olefins, which are capable of reacting with the alkanol by yielding an ether. Further, it is the amount of such olefins in the fresh feed of the process that is considered. By recirculating a sidedraw from the first distillation column, the isoolefin concentration can be maintained at a low level in the first reaction zone, which reduces the extent of side reactions and helps to keep the temperatures low.

By contrast, when the known process is used for dimerizing an olefinic hydrocarbon feedstock, the fresh olefinic hydrocarbon feedstock is fed to the reaction zone of the system, the olefinic hydrocarbon feedstock is contacted with the acidic catalyst in the presence of an oxygenate at conditions in which at least a part of the olefins dimerizes, i.e. at a ratio of the oxygenate to olefin in the first stage of 0.01-0.7, the effluent from said reaction zone is conducted to the distillation zone where dimerized reaction product is separated from said effluent, and at least a part of one flow comprising oxygenate is withdrawn from the side of at least one distillation column and recycled to dimerization. The reaction mixture is recovered and optionally hydrogenated to form a parafinic reaction product.

The present invention therefore comprises operating the above process as described in the latter embodiment during a first predetermined period of time for producing dimers and as described in the former embodiment during a second predetermined period of time for producing alkyl ethers.

According to another aspect of the invention, a novel process is provided. That process comprises production of alkyl ethers by etherification of tertiary $C_{4-7}$ olefins with an alkanol, comprising carrying out the etherification in reactor train system primarily configured for dimerization of isoolefins.

More specifically, the process according to the present invention for producing alkyl ethers is mainly characterized by what is stated in the characterizing parts of claims 1 and 4.

The process for producing alkyl ethers is characterized by what is stated in the characterizing part of claim 5, and the method of converting a dimerization process into an etherification process is characterized by what is stated in the characterizing part of claim 14.

Considerable advantages are obtained by the present invention. Thus, the investment costs are low for converting a dimerization process according to the basic concept of EP-A-0 994 088 into a combined dimerization/etherification process. The apparatus used in the dimerization process can be used as such, and there is no need for buying a reactive distillation column, as required in some of the commercial etherification processes.

Generally, and importantly, the invention makes it possible to change the product of the process from dimer to ether and vice versa merely by adjusting specific flows within the process. The present kind of process is therefore readily adaptable to fluctuating market demands for various gasoline octane-boosters (isooctane or MTBE).

Basically, the present invention allows for the production of ethers or dimerized products in a process primarily configured for dimerization of isoolefins, such as a hydrocarbon feedstock containing isobutene, by only minor changes in the conditions of operation.

DETAILED DESCRIPTION OF THE INVENTION

Definitions

Figure 1:
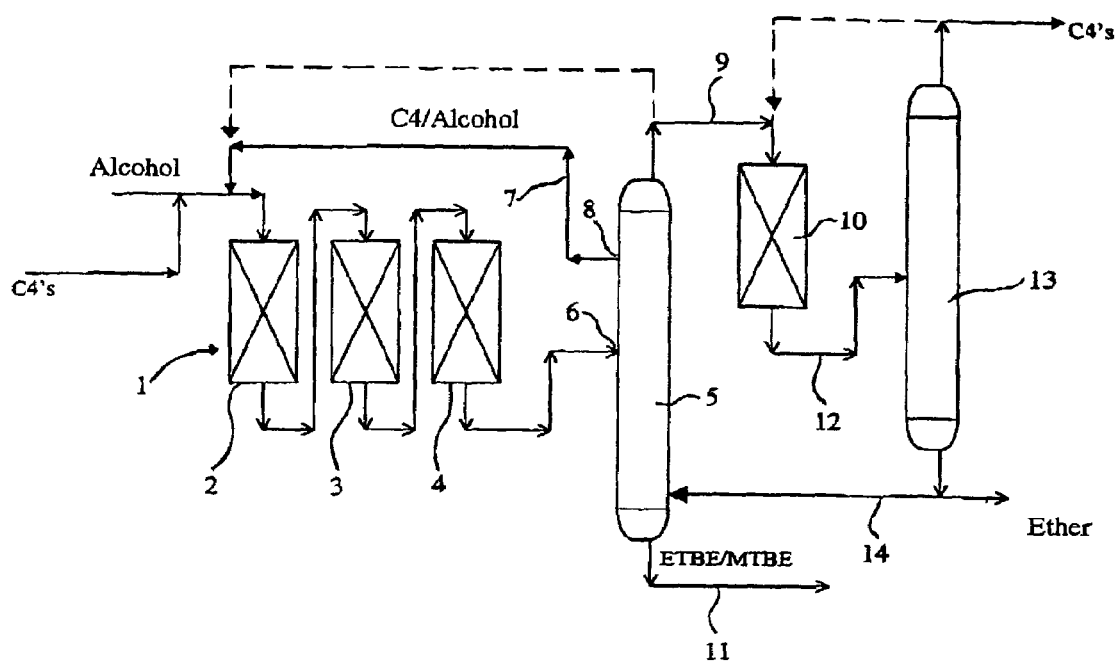
FIG. 1 shows in a schematic fashion the simplified configuration of a process according to a first embodiment of the present invention for preparing a product containing tert-methyl butyl ether or tert-ethyl butyl ether, or dimers, such as isooctane or isooctene.

For the purposes of the present invention, "distillation zone" designates a distillation system comprising one or more distillation columns. In the case of a plurality of columns, they are preferably connected in series. The feed plate can be selected for each column to be most advantageous in view of the overall process. Likewise, the plates for the side-draw of flows to be recovered or circulated can be selected individually for each column. The distillation column can be any column suitable for distillation, such as a packed column, or one provided with valve, sieve or bubble-cap trays.

A "reaction zone" comprises at least one, typically two or three, reactor(s). The reactor can be, e.g., a tubular reactor with multiple pipes, wherein the pipes are filled with catalyst. Other possibilities include a simple tubular reactor, a boiler reactor, a packed bed reactor and a fluidized bed reactor. The reactor used is preferably such in which the catalyst is placed in more than one layer and cooling is introduced between the layers. Preferably at least one of the reactors has a cooling system. For example, the pipes of the tubular reactor with multiple pipes can be cooled. Another example of a suitable reactor is a combination of a fixed bed reactor and a cooler, in which part of the reactor effluent can be circulated back to the reactor via the cooler. The operating pressure of the reactors depends on the type of the reactor and on the composition of the feed, typically it is desired to keep the reaction mixture in liquid phase.

"Alkanol" stands for the same as "alkyl alcohol". The alkanols used in the present invention include primary, secondary and tertiary alcohols, such as methanol, ethanol, propanol, 2-propanol, and the various butanols (i-, n- and t-butanol). Even heavier alkanols are possible, although their reactivity with the isoolefin is generally lower.

"Etherification" means a reaction between an alkanol and an olefin, in particular an isoolefin, to produce an ether. When only $C_4$-olefins are fed to the process, the resulting product of the etherification comprises tert-methyl or tert-ethyl butyl ether (abbreviated "MTBE" and "ETBE", respectively). However, when both $C_4$- and $C_5$-olefins are present in the feed, there is formed a mixture of MTBE or ETBE and heavier ethers, such as TAME (tert-amyl methyl ether) or TAEE (tert-amyl ethyl ether).

"Dimerization" means a reaction in which two olefin molecules are reacted with each other to form a dimer, in the case of $C_4$-olefins "isooctene" (cf. below). When the hydrocarbon feedstock contains both $C_4$ and $C_5$ olefins, the reaction product comprises dimers of both of these. However, in addition to dimerization, also reactions between $C_4$-olefins and $C_5$-olefins yielding $C_9$-olefins can occur. The word "dimer" is used for the reaction products in the specification for reasons of simplicity, but it is to be understood that when both $C_4$- and $C_5$-olefins are present in the feed, the reaction mixture typically contains also some amount of the $C_9$-olefins.

"Isooctene" and "diisobutene" are both products of isobutene dimerization. Thus, they can be used interchangeably to designate 2,4,4-trimethyl-1-pentene and 2,4,4-trimethyl-2-pentene or a mixture thereof.

The "reactive isoolefins" which take part in the etherification reactions include, for example, the following compounds: isobutylene, 2-methyl-1-butene, 2-methyl-2-butene, 2-methyl-1-pentene, 2-methyl-2-pentene, 2,3-dimethyl-1-butene, 2,3-dimethyl-2-butene, 2-ethyl-1-butene, 2-methyl-2-hexene, 2,3-dimethyl-1-pentene, 2,3-dimethyl-2-pentene, 2,4-dimethyl-1-pentene, 2-ethyl-1-pentene and 2-ethyl-2-pentene.

The Overall Process

In the following, the production of ethers will first be examined in more detail.

According to the present invention, an olefinic hydrocarbon feedstock is fed into a reactor train system including at least one primary reaction zone, at least one primary distillation zone connected to an effluent outlet of the primary reaction zone, at least one secondary reaction zone connected to an overhead draw of the distillation zone, and at least one secondary distillation zone connected to the effluent outlet of the secondary reaction zone. During starting up of the process, the feed is formed by fresh feed, but during continuous operation of the process, the olefinic hydrocarbon feedstock comprises partly fresh feed and partly a recirculated stream from the first distillation zone, as will be explained below. The fresh feedstock contains at least one isoolefin selected from the group of tertiary $C_{4-7}$ olefins, in particular the isoolefin is selected from isobutenes and isopentenes and mixtures thereof. The olefinic hydrocarbon feedstock is contacted in the primary reaction zone with an acidic catalyst in the presence of from 50 mole-% to about a stoichiometric amount of an alkanol, calculated from the amount of tertiary $C_{4-7}$ olefins, at conditions in which at least a part of the olefins are etherified.

Typically, the feed comprises $C_4$-olefins, preferably isobutene, or $C_5$-olefins, preferably isoamylene. The feed can consist of pure isobutene, but in practice, the feedstock readily available comprises $C_4$-based hydrocarbon fractions from oil refining. Preferably, the feed comprises a fraction obtained from isobutane dehydrogenation, when the feed comprises mainly isobutene and isobutane and possibly small amounts of $C_3$- and $C_5$-hydrocarbons. Typically the feed then comprises 40-60 wt-% of isobutene and 60-40 wt-% isobutane, usually there is 5-20% less isobutene present than isobutane. Thus, the ratio of isobutene to isobutane is approximately 4:6 . . . 5:5.5. As an example of an isobutane dehydrogenation fraction, the following can be presented: 45 wt-% isobutene, 50 wt-% isobutane and other inert $C_4$-hydrocarbons and approximately 5 wt-% of $C_3$-, $C_5$- and heavier hydrocarbons altogether.

Due to the high isobutene content in the flow from the isobutane dehydrogenation the amounts of inert hydrocarbons in the recycling flows remain relatively small.

Suitable hydrocarbon feedstocks for preparing tertiary alkyl ethers are, for example, the following: FCC gasoline, FCC light gasoline, FCC liquefied petroleum gas, Pyrolysis $C_5$ gasoline, $C_4$ stream (Raffinate 1) from a steam cracking unit, olefnic $C_4$ stream from a butane dehydrogenating unit, TCC gasoline, $C_4$ stream from TCC, RCC gasoline, $C_4$ stream from RCC, coker gasoline or $C_4$ stream originating from a coking unit or a mixture of these.

Before the etherification reaction, the hydrocarbon feedstock can be subjected to a pretreatment in order to remove impurities and to increase the amount of reactive isoolefins. Acidic residues can be removed by washing the feedstock with water and multi-unsaturated olefins can be selectively hydrogenated in the presence of a catalyst to form mono-unsaturated compounds.

According to the present invention, an alcohol, preferably $C_1$-$C_6$ alcohol (e.g. methanol, ethanol, isopropanol or t-butanol) is used for etherification. The alcohol can be a primary, secondary or tertiary alcohol or a mixture thereof. Further examples include tert-amyl methylether, 2-butanol and 2-pentanol. Oxygenates, such as alcohol, protect the catalyst by hindering poisoning and the formation of large molecules, since the heavier components forming from trimers and tetramers block the catalyst. The molar ratio of the oxygenate and olefin, e.g., alcohol and isobutene, in the feed is at least 0.7, preferably in excess of 0.75 and up to about 1.2. In particular, it is close to the stoichiometric ratio, such as about 0.8 to 1.0.

The ratio of alcohol to olefin can be separately adjusted in the two reaction zones, the primary and the secondary reaction zones.

The hydrocarbon feed containing olefins is contacted with a catalyst together with alcohol in the reaction zone. The catalyst is preferably arranged in a solid bed. According to the invention, an acidic catalyst is used. Preferably, ion-exchange resins are used, for example such as are used for etherification. As catalysts can, however, be used zeolites and other inorganic catalysts. Thus, the resin can comprise sulphonic acid groups and it can be prepared by polymerizing or copolymerizing aromatic vinyl compounds and, thereafter, sulphonating. As examples of aromatic vinyl compounds the following may be mentioned: styrene, vinyl toluene, vinyl naphthalene, vinyl ethyl benzene, methyl styrene, vinyl chlorobenzene, and vinyl xylene. An acidic ion-exchange resin contains typically approximately 1.3 . . . 1.9, even up to 2 sulphonic acid groups per an aromatic group. Preferred resins are those based on copolymers of aromatic monovinyl compounds and aromatic polyvinyl, in particular divinyl, compounds, in which the concentration of polyvinylbenzene is approximately 1 . . . 20 wt-% of the copolymer. The particle size of the ion-exchange resin is preferably approximately 0.15 . . . 1 mm.

In addition to the resins already described, also perfluorosulphonic acid resins consisting of copolymers of sulphonylfluorovinyl ethyl and fluorocarbon compounds can be used.

Various suitable ion-exchange resins are commercially available, an example of these is Amberlyst 15.

The concentration of the catalyst is typically 0.01-20%, preferably approximately 0.1-10% of the weight of the liquid mixture to be handled.

The temperature of the reaction zone is typically 50-120° C. The upper level of the temperature range is set by the heat-resistance properties of the catalyst. The reaction can very well be carried out at temperatures higher than 120° C., for example up to 160° C. or even higher. Lower temperature favours the formation of ether.

The reaction effluent is conducted from the primary reaction zone to the primary distillation zone, wherein the etherification reaction product is separated from the effluent. In the primary distillation zone, at least one flow comprising unreacted olefins and alkanol is withdrawn from the side of a (the) distillation column and recirculated from the distillation zone back to the primary reaction zone. With the help of the sidedraw the conversion of the etherification process is increased. It is to be understood, that although the following description refers to a sideflow in singular, which is the typical configuration, it is also possible to withdraw two or more sideflows containing oxygenate and circulate all those flows back to etherification.

The sidedraw is typically taken from a plate higher than the feed plate. The sidedraw is circulated back to dimerization. The amount of the circulated flow can be altered as well as the point to which it is conducted (for example, either to the reaction zone or to the fresh feed). The mass flow of the circulated flow is typically 0.01 ... 10 times, preferably 1 ... 5, in particular 0.3 . . . 2, times the mass flow of fresh hydrocarbon feed.

The conversion rate in the first reaction zone is rather high, preferably over 85 mole-% with respect to the isoolefinic feed, in particular over 90 mole-%, preferably over 95 mole-%.

The overhead of the primary distillation zone, which comprises merely unreacted isoolefins, is conducted to the secondary reaction zone, a postreactor or a cascade of reactors, in which the conversion rate is increased to in excess of 98 mole-%, to close to 99 mole-% or even over. Thus, the conversion rate in the second reaction zone is typically at least 95 mole-%. In the second reaction zone, the unreacted isoolefins are contacted with with an acidic catalyst in the presence of an alkanol to etherify the isoolefins. The alkanol is either separately fed to the second reaction zone, or it is included in the overhead product of the first distillation zone.

The effluent of the second reaction zone is conducted to the secondary distillation zone, in which the etherified product of the secondary reaction zone is separated from the unreacted olefins. The isoolefin ethers are recovered from the bottom of the primary and secondary distillation zones and optionally the bottoms products are combined. The overhead of the second distillation process can be conducted to a traditional methanol or ethanol recovery unit, where the alcohol can be removed by water washing and distillation. It is also possible to recirculate the overhead to the first reaction zone where it is combined with fresh feed or with the sidedraw circulated from the first distillation zone.

The etherified reaction product is obtained as the bottoms product from the first distillation zone.

The overhead of the distillation zones can be partially recycled to the feed of the reaction zones. In particular, in this way diluents, such as unreacted C3 to C8 hydrocarbons, can be separated from the overhead (C4s) streams and recycled. Typically, the diluents of the overhead of the second distillation zone are recycled to the second reaction zone, and the diluents of the overhead of the first distillation zone are recycled to the first reaction zone.

The recycled flow comprises about 1 to 90 mole-%, preferably about 5 to 80 mole-% of the overhead stream.

Similarly, it is possible to recycle a part, such as 0.1 to 60 mole-%, typically 1 to 50 mole-%, of the effluent of the reaction zones to the feed of reaction zones. By recycling various (inert/unreacted) hydrocarbons, it becomes possible effectively to control the temperature rise in the process. This is important in particular when the process/apparatus are used for producing ethers.

As indicated above, practically the same process configuration can be used for preparing dimers. In that case, the hydrocarbon feed containing olefins is contacted with the catalyst together with the alcohol or another oxygenate, such as water, in the primary reaction zone at conditions in which at least a part of the olefins is dimerized. In case where the olefin feed comprises both $C_4$- and $C_5$-olefins, also reactions between different olefins occur, thus forming $C_9$-olefins. In addition also small amounts of other oligomers, such as trimers or tetramers are formed in the reaction. The flow from the reaction zone is introduced into a distillation zone, where the main part of the dimerized reaction product is separated.

For producing the dimer, the ratio of alkanol-to-olefin being less than 0.7, calculated from the amount of tertiary $C_{4-7}$ olefins of the fresh feedstock, at conditions in which at least a part of the olefins are dimerized.

The dimerization process can be carried out in two reaction stages, of which in the first stage the ratio of oxygenate to olefin is higher and the residence time reduced in the reactor, and in the second stage the ratio of oxygenate to olefin is low in the reactor and the residence time is longer. The ratio of oxygenate to olefin in the first stage is 0.01-0.7 and in the second stage 0.001-0.5, in particular the ratio of oxygenate to olefin in the first stage is 0.01-0.15 and in the second stage 0.001-0.1.

The residence time of the present invention (for producing ethers and for producing dimers) is generally about 1 (VHSV), typically 0.1 to 10, in particular about 0.5 to 5 $h^{-1}$. In the two reaction stage option mentioned above, the residence time in the first stage employing higher oxygen to olefin ratios is generally higher than one (up to 5 or up to 2) and in the second stage it is 1 or less (down to about 0.5).

A sidedraw comprising alcohol, other oxygenate and/or the reaction product is circulated from the distillation zone back to the reaction zone. With the help of the sidedraw the conversion of the olefin and the production of dimerized product is increased. When using alcohol, which does not significantly react with the olefin (such as TBA), the sidedraw comprises a major part of the alcohol present in the reactor effluent. When using alcohol, which does react with the olefin (such as methanol with isobutene), the sidedraw can comprise both alcohol and ether. Typically the sidedraw comprises alcohol up to 80 wt-%, typically 10-50 wt-%, depending on pressure and hydrocarbons.

The flow from the reaction zone is conducted to the first distillation zone, where the components are separated from each another. The conversion rate can be increased by conducting the unreacted isoolefins to the second reaction zone, as explained above.

The operation of the process for producing dimers is explained in more detail in EP-A-0 994 088. Basically, the process is switched over to the desired product merely by increasing or decreasing the ratio of alcohol (or oxygenate) to isoolefin in the reaction zones to produce either ether or dimer. The operation of the process can be carried out in "campaigns", such that during a first predetermined period of time, ranging from 1 day to 6 months, or more, the process is used for producing dimers according to the embodiment described above, and—depending on the demand, then adjusted for productiong of alkyl ethers during a second predetermined period of time, likewise ranging from about 1 day to 6 months, or more.

A preferred process reconfiguration for etherifiction is presented in the following.

According to the embodiment of FIG. 1, the olefins are etherified in a process comprising a primary reaction zone 1, having three reactors 2-4 arranged in a cascade. The outlet of the last reactor 4 is connected to a first distillation column 5 and fed into the column at a feed point 6. From the column, a side stream 7 is withdrawn at a point 8 above the feed point. The sidedraw, which comprises $C_4$ olefins and alcohol, is circulated to the primary reaction zone 1 and combined with the fresh olefinic feed before the inlet nozzle of the first reactor 2. The overhead stream 9 of the distillation column 5 is conducted to a secondary reactor 10. The bottoms product 11, comprising pure ether, is recovered.

The secondary reactor 10 is basically similar to the primary reactors 2 to 4, although it can be of smaller size (contain a smaller catalyst bed). The reactor effluent 12 of the secondary reactor is conducted to a secondary distillation column 13, wherein the alcohol is distilled off and taken to further treatment, whereas the bottoms product, which comprises the alkyl ether, is withdrawn and fed into the first distillation column 5. The second distillation column can also be operated in such a way that an essentially pure (ether) product is obtained and separately recovered, as shown by the arrow pointing to the right in the drawing.

The process configuration according to FIG. 1 differs from the ones disclosed in U.S. Pat. Nos. 5,536,886, 5,637,777, 5,908,964, and 6,369,280 in the sense that the overhead product of the first distillation zone does not comprise an azeotropic composition of alcohol and hydrocarbons. Since a dimerization process is provided with suitable equipment for recovery of alcohol, it is not necessary to restrict the amount of alcohol withdrawn from separation. By using the sidedraw, it is possible to dilute the process feed with respect to the olefins to obtain the proper ratio to fit a high conversion rate of ethers.

The following, non-limiting examples describes the production of ethers. Corresponding embodiments describing the production dimers can be found in EP-A-0 994 088.

EXAMPLE 1

A feed containing mainly $C_4$ hydrocarbons and methanol is fed to a process according to the present invention, having the process configuration described in FIG. 1 with the exception that all the bottom product (BOT2) of the second column is fed into the first column. Table I presents the calculated mass balances.

TABLE I

|  | C4 FEED | MEOH | REAC 1 | BOT 1 | RECYCLE | DIST 1 | REAC 2 | BOT 2 | DIST 2 |
|---|---|---|---|---|---|---|---|---|---|
| C4− | 0.17 | 0.00 | 0.11 | 0.00 | 0.06 | 0.28 | 0.28 | 0.00 | 0.29 |
| ISOBUTENE | 39.98 | 0.00 | 1.38 | 0.21 | 2.15 | 1.65 | 0.05 | 0.00 | 0.05 |
| INERT C4 | 59.56 | 0.00 | 65.29 | 1.81 | 96.06 | 95.63 | 95.63 | 4.97 | 98.09 |
| MEOH | 0.00 | 99.95 | 0.90 | 0.00 | 0.33 | 2.45 | 1.53 | 0.00 | 1.57 |
| C5+ | 0.28 | 0.00 | 0.14 | 0.42 | 0.01 | 0.00 | 0.00 | 0.00 | 0.00 |
| MTBE | 0.00 | 0.00 | 31.99 | 96.92 | 1.39 | 0.00 | 2.51 | 95.00 | 0.00 |
| TAME | 0.00 | 0.00 | 0.01 | 0.04 | 0.00 | 0.00 | 0.00 | 0.00 | 0.00 |
| DIB | 0.01 | 0.00 | 0.18 | 0.53 | 0.00 | 0.00 | 0.00 | 0.03 | 0.00 |
| TBA | 0.00 | 0.00 | 0.00 | 0.07 | 0.01 | 0.00 | 0.00 | 0.00 | 0.00 |
| H2O | 0.00 | 0.05 | 0.01 | 0.00 | 0.00 | 0.00 | 0.00 | 0.00 | 0.00 |
| Flow rate, kg/h | 30 | 7.0 | 57.6 | 19.2 | 20.5 | 18.3 | 18.3 | 0.5 | 17.9 |

C4− hydrocarbons having less than 4 carbon atoms
INERT C4 saturated C4's and other C4 hydrocarbons, which do not take part in etherification and dimerization
C5+ hydrocarbons (saturated and unsaturated) which contain at least 5 carbon atoms
MEOH methanol
MTBE methyl-tertiary butyl ether
TAME tertiary amyl methyl ether
DIB diisobutene
TBA tertiary butyl alcohol

EXAMPLE 2

A feed containing mainly $C_4$ hydrocarbons and water is fed to a process described in FIG. 1 with the exception that all the bottom product (BOT2) of the second column is fed into the first column. Table II presents the calculated mass balances.

TABLE II

|  | C4 FEED | WATER | REAC 1 | BOT 1 | RECYCLE | DIST 1 | REAC 2 | BOT 2 | DIST 2 |
|---|---|---|---|---|---|---|---|---|---|
| C4− | 0.17 | 0.00 | 0.13 | 0.00 | 0.06 | 0.24 | 0.24 | 0.00 | 0.28 |
| ISOBUTENE | 39.98 | 0.00 | 6.98 | 0.00 | 8.43 | 8.55 | 0.88 | 0.88 | 0.88 |
| INERT C4 | 59.56 | 0.00 | 69.26 | 0.00 | 83.65 | 91.10 | 91.07 | 49.05 | 98.79 |
| C5-C7 | 0.28 | 0.00 | 0.65 | 0.60 | 1.24 | 0.00 | 0.00 | 0.01 | 0.00 |
| DIB | 0.01 | 0.00 | 19.28 | 93.91 | 0.03 | 0.00 | 6.96 | 44.81 | 0.00 |
| C8+ | 0.00 | 0.00 | 1.01 | 5.49 | 0.00 | 0.00 | 0.68 | 4.39 | 0.00 |
| TBA | 0.00 | 0.00 | 2.61 | 0.00 | 6.57 | 0.00 | 0.13 | 0.86 | 0.00 |
| H2O | 0.00 | 100.00 | 0.08 | 0.00 | 0.01 | 0.11 | 0.04 | 0.00 | 0.05 |
| Flow rate, kg/h | 30.00 | 0.04 | 50.58 | 11.96 | 20.54 | 21.38 | 21.37 | 3.32 | 10.16 |

C4− hydrocarbons having less than 4 carbon atoms
INERT C4 saturated C4's and other C4 hydrocarbons, which do not take part in etherification and dimerization
C5-C7 hydrocarbons (saturated and unsaturated) which contain 5 to 7 carbon atoms
C8+ hydrocarbons (saturated and unsaturated) which contain at least 8 carbon atoms
MEOH methanol
MTBE methyl-tertiary butyl ether
TAME tertiary amyl methyl ether
DIB diisobutene
TBA tertiary butyl alcohol

The invention claimed is:

1. A process for producing gasoline fuel components comprising alkyl ethers and dimers of tertiary olefins from an olefinic feed containing tertiary $C_{4-7}$ olefins with an acidic catalyst in the presence of alkanol in a reactor train system including
   at least one primary reaction zone with an olefin inlet and an effluent outlet,
   at least one primary distillation zone connected to the effluent outlet of the primary reaction zone, said distillation zone having an overhead draw,
   at least one secondary reaction zone connected to the overhead draw of the distillation zone and having an effluent outlet, and
   at least one secondary distillation zone connected to the effluent outlet of the secondary reaction zone,
wherein at least one flow comprising unreacted olefins and alkanol is withdrawn from the side of the primary distillation zone and said flow is circulated from said distillation zone back to the primary reaction zone, said process comprising producing in the same reactor train system
   dimers during a first period of time by contacting the hydrocarbon feedstock with the acidic catalyst in the presence of alkanol at an alkanol-to-olefin molar ratio of less than 0.7, calculated from the amount of tertiary $C_{4-7}$ olefins of the fresh feedstock, at conditions in which at least a part of the olefins are dimerized, and
   alkyl ether during a second period of time by contacting the hydrocarbon feedstock with the acidic catalyst in the presence of alkanol at an alkanol-to-olefin molar ratio of 0.7 to 2, calculated from the amount of tertiary $C_{4-7}$ olefins of the fresh feedstock, at conditions in which at least a part of the olefins are etherified.

2. The process according to claim 1, wherein the ratio of oxygenate to olefin in the first stage is 0.01-0.7 and in the second stage 0.001-0.5.

3. The process according to claim 1, wherein the overhead of at least one of the distillation zones is partially recycled to the feed of one of the reaction zones.

4. The process according to claim 3, comprising recycling unreacted $C_3$ to $C_8$ hydro-carbons from the overhead of a distillation zone to a reaction zone.

5. The process according to claim 1, wherein a part of the effluent of at least one of the reaction zones is recycled to the feed of at least one reaction zone.

6. The process according to claim 1, wherein the mole ratio of alkanol to reactive olefin is in excess of 0.9 up to about 1.1.

7. The process according to claim 1, wherein the conversion rate is at least 90 mole-% with respect to the reactive olefins after the first reaction zone, and in excess of 98 mole-% after the second reaction zone.

8. The process according to claim 1, wherein at least a part of the etherified isoolefins of the process are recovered in the form of the bottom product of the first distillation zone.

9. The process according to claim 8, wherein the bottom product of the second distillation zone is fed to the first distillation zone.

10. The process according to claim 1, wherein at least a part of the etherified isoolefins of the process are recovered in the form of the bottom product of the second distillation zone.

11. The process according to claim 1, wherein the feed comprises isobutene and isopentene or a mixture thereof and the alkanol comprises methanol or ethanol.

12. The process according to claim 11, wherein tert-methyl butyl ether is produced.

13. The process according to claim 1 or 11, wherein isooctene or, subject to hydrogenation, isooctane is produced.

14. The process according to claim 2, wherein the ratio of oxygenate to olefin in the first stage is 0.01-0.15 and in the second stage 0.001-0.1.

15. The process according to claim 1, wherein the sidedraw is taken from a plate higher than the feed plate.

16. The process according to claim 15, wherein the mass flow of the circulated flow is 0.01 to 10 times the mass flow of fresh hydrocarbon feed.

17. The process according to claim 16, wherein the mass flow of the circulated flow is 1 to 5 times the mass flow of fresh hydrocarbon feed.

18. The process according to claim 16, wherein the mass flow of the circulated flow is 0.3 to 2 times the mass flow of fresh hydrocarbon feed.

* * * * *